US006756390B2

(12) United States Patent
Cho et al.

(10) Patent No.: US 6,756,390 B2
(45) Date of Patent: Jun. 29, 2004

(54) ORGANIC ACID SALT OF AMLODIPINE

(75) Inventors: Seong Hwan Cho, Suwon-si (KR); Yong Sik Youn, Yongin (KR); Yun Taek Jung, Seoul (KR); Choong Sil Park, Icheon-si (KR); Hyuk Koo Lee, Yongin-si (KR); Kwang Hyeg Lee, Seongnam-si (KR); Eun Ju Jeong, Chungcheongbuk-do (KR); Young Hoon Kim, Seoul (KR); Hae Tak Jin, Yongin-si (KR); Jun Hee Cheon, Suwon-si (KR); Sung Hak Lee, Yongin-si (KR); Sung Hak Jung, Seoul (KR); Dong Kwon Lim, Seongnam-si (KR); Kyu Jeong Yeon, Yongin-si (KR); Yun Cheul Kim, Seoul (KR); Kyung Mi Park, Seoul (KR); Hyun Suk Kang, Seoul (KR)

(73) Assignee: CJ Corp., Seoul (KR)

( * ) Notice: Subject to any disclaimer, the term of this patent is extended or adjusted under 35 U.S.C. 154(b) by 0 days.

(21) Appl. No.: 10/628,210

(22) Filed: Jul. 29, 2003

(65) Prior Publication Data

US 2004/0029923 A1 Feb. 12, 2004

(30) Foreign Application Priority Data

Jul. 30, 2002 (KR) .............................. 10-2002-0044857

(51) Int. Cl.$^7$ ...................... A61K 31/44; C07D 405/00
(52) U.S. Cl. .................... 514/336; 546/284.4
(58) Field of Search ....................... 546/284.4; 514/336

(56) References Cited

U.S. PATENT DOCUMENTS

| 4,572,909 A | 2/1986 | Campbell et al. |
| 4,758,569 A | 7/1988 | Swindell |
| 4,879,303 A | 11/1989 | Davison et al. |
| 6,291,490 B1 | 9/2001 | Young |

FOREIGN PATENT DOCUMENTS

| EP | 0089167 | 9/1983 |
| KR | 95-7228 | 4/1989 |
| KR | 19912145 | 4/1989 |
| WO | 99/52873 | 10/1999 |

*Primary Examiner*—Amelia A. Owens
(74) *Attorney, Agent, or Firm*—Greenblum & Bernstein, P.L.C.

(57) ABSTRACT

Disclosed are a novel organic acid salt of amlodipine with superb physicochemical properties, its preparation method, and a pharmaceutical composition containing the same as a therapeutically active ingredient.

10 Claims, No Drawings

ORGANIC ACID SALT OF AMLODIPINE

BACKGROUND OF THE INVENTION

1. Field of the Invention

The present invention relates to a novel organic acid salt of amlodipine (2-[(2-aminoethoxy)methyl]-4-(2-chlorophenyl)-1,4-dihydro-6-methyl-3,5-pyridinedicarboxylic acid 3-ethyl 5-methyl ester), represented by the following chemical formula 1, its preparation method, and a pharmaceutical composition containing the same as an effective ingredient.

[Chemical Formula 1]

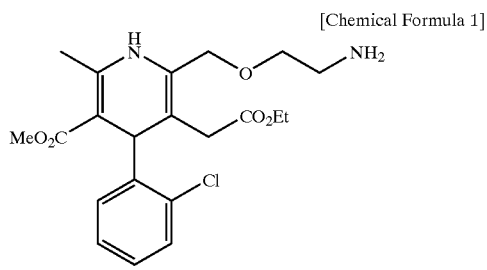

2. Description of the Prior Art

With activity to block calcium channels in the body, amlodipine is used for the treatment of hypertension. This calcium channel blocker is found in many prior arts.

European Pat. Laid-Open Publication No. 89,167 discloses acid salts of amlodipine which can be formed from acids which may form nontoxic acid addition salts with pharmaceutically acceptable anions, such as hydrochloride, hydrobromide, sulfate, phosphate, acetate, maleate, fumarate, lactate, tartrate, citrate, gluconate, etc.

U.S. Pat. No. 6,291,490 introduces a pharmaceutical composition containing as an active ingredient S-(−)-amlodipine which possesses potent activity in treating both systolic and diastolic hypertension while avoiding adverse effects associated with administration of the racemic mixture of amlodipine.

Both U.S. Pat. No. 4,879,303 and Korean Pat. Laid-Open Publication No. 1989-3375 disclose amlodipine besylate, saying that amlodipine besylate is superior over other salts of amlodipine, such as hydrochloride, acetate and mesylate in physicochemical properties including (1) solubility, (2) stability, (3) non-hygroscopicity, and (4) processability for tablet formulation.

However, since amlodipine besylate in current use is relatively low in solubility at pH 1–7.4, there is a need for novel salts which are of sufficient solubility, so as to increase the bioavailability of amlodipine and easily formulate its injections. Additionally, amlodipine besylate has been found to be sensitive to light. Therefore lysates are generated when the salt is exposed to light.

Further, amlodipine besylate is disadvantageous due to benzene sulfonic acid being used in its production process. That is, benzene sulfonic acid is difficult to industrially treat because it is corrosive and toxic. In addition, its high hygroscopicity requires special procedures for its transport, delivery and use. Another disadvantage is that the water content of benzene sulfonic acid is too high, amounting to about 10%. In order to avoid these problems, ammonium benzene sulfonate is employed as an alternative, but with concomitant generation of ammonia gas. This method needs additional processes for absorbing and inactivating ammonia gas (PCT Publication No. WO1999/52873).

By contrast, tetrahydro-5-oxo-2-furancarboxylic acid (commercially available as purity 98% or higher) is non-toxic to the body and is easy to handle in preparing amlodipine tetrahydro-5-oxo-2-furancarboxylate.

DISCLOSURE OF THE INVENTION

Leading to the present invention, the intensive and thorough research into therapeutically effective organic acid salts of amlodipine, conducted by the present inventors aiming to overcome the problems encountered in prior arts, resulted in the finding that amlodipine tetrahydro-5-oxo-2-furancarboxylate has excellent physicochemical properties including solubility, non-hygroscopicity, chemical and light stability, and processability for dosage formation, as well as the fact that tetrahydro-5-oxo-2-furancarboxylic acid(TOF acid) is less toxic and corrosive than benzene sulfonic acid so that the amlodipine tetrahydro-5-oxo-2-furancarboxylate is industrially and medically useful.

Therefore, it is an object of the present invention to provide a tetrahydro-5-oxo-2-furancarboxylic acid salt of amlodipine.

It is another object of the present invention to provide a method for preparing a tetrahydro-5-oxo-2-furancarboxylic acid salt of amlodipine.

It is a further object of the present invention to provide a pharmaceutical composition containing the tetrahydro-5-oxo-2-furancarboxylic acid salt of amlodipine as a therapeutically active ingredient.

In accordance with an aspect of the present invention, there is provided a tetrahydro-5-oxo-2-furancarboxylic acid salt of amlodipine, preferably a light-stable tetrahydro-5-oxo-2-furancarboxylic acid salt of amlodipine, more preferably amlodipine (S)-tetrahydro-5-oxo-2-furancarboxylate or amlodipine (R)-tetrahydro-5-oxo-2-furancarboxylate, and most preferably a crystalline tetrahydro-5-oxo-2-furancarboxylic acid salt of amlodipine.

In accordance with another aspect of the present invention, there is provided a method for preparing a tetrahydro-5-oxo-2-furancarboxylate acid salt of amlodipine, in which amlodipine is reacted with tetrahydro-5-oxo-2-furancarboxylic acid and preferably with (S)-tetrahydro-5-oxo-2-furancarboxylic acid or (R)-tetrahydro-5-oxo-2-furancarboxylic acid in an inert solvent.

In accordance with a further aspect of the present invention, there is provided a pharmaceutical composition effective for the treatment of ischemic cardiac disorders or hypertension, comprising a therapeutically effective amount of amlodipine tetrahydro-5-oxo-2-furancarboxylate and a pharmaceutically acceptable diluent or carrier preferably in the dosage form of tablets, capsules, solutions or injectables.

DETAILED DESCRIPTION OF THE INVENTION

The present invention encompasses amlodipine tetrahydro-5-oxo-2-furancarboxylate, represented by the following chemical formula 2.

[Chemical Formula 2]

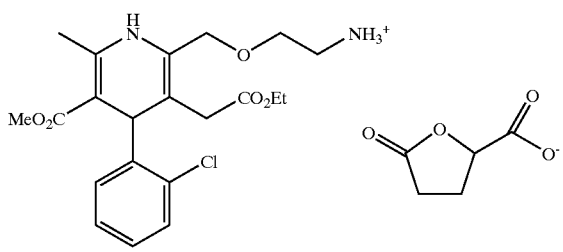

Compared to commercially available amlodipine besylate, amlodipine tetrahydro-5-oxo-2-furancarboxylate exhibits equal or better non-hygroscopicity, formulation processability and chemical stability and especially, at least 400 times greater solubility in distilled water or under various pH conditions. Accordingly, with the feasibility of being formulated into soultions and injectables as well as the difficulty of being precipitated in blood, the amlodipine tetrahydro-5-oxo-2-furancarboxylate of the present invention is of great bioavailability. An extraordinary improvement in stability to light is found in the tetrahydro-5-oxo-2-furancarboxylate over other known organic acid salts, so that it can be stably stored for a long period of time without losing the medicinal effect as an anti-hypertensive agent upon long-term medicine-taking.

The present invention also encompasses light-stable amlodipine tetrahydro-5-oxo-2-furancarboxylate. The term "light-stable" as used herein means that after the salt is stored for 4 weeks at 25° C. with exposure to daylight, its mass is maintained at 90% or more of the original mass, preferably at 95% or more, and more preferably at 98% or more.

Tetrahydro-5-oxo-2-furancarboxylic acid suitable for the preparation of the amlodipine tetrahydro-5-oxo-2-furancarboxylate of the present invention may be a racemic mixture or an optically pure material with preference to an optically pure material, that is, (S)-tetrahydro-5-oxo-2-furancarboxylic acid or (R)-tetrahydro-5-oxo-2-furancarboxylic acid.

Tetrahydro-5-oxo-2-furancarboxylic acid salts of amlodipine according to the present invention may be in a crystalline form or an amorphous form with preference to a crystalline form.

The present invention also encompasses a method for preparing tetrahydro-5-oxo-2-furancarboxylic acid salts of amlodipine. The salts can be prepared by reacting amlodipine with tetrahydro-5-oxo-2-furancarboxylic acid in an inert solvent, as seen in the following reaction formula 1.

[Reaction Formula 1]

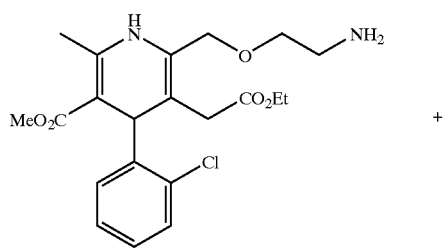

+

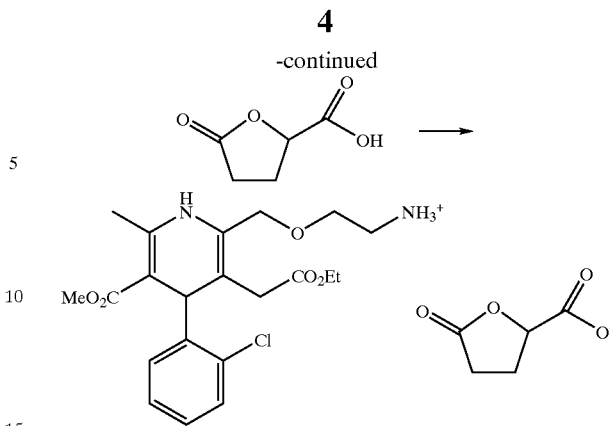

Tetrahydro-5-oxo-2-furancarboxylic acid may be a racemic mixture, preferably an optically pure compound, that is, (S)- or (R)-tetrahydro-5-oxo-2-furancarboxylic acid, and more preferably, (S)-tetrahydro-5-oxo-2-furancarboxylic acid which can be economically synthesized from monosodium L-glutamate (MSG) or L-glutmaic acid.

Tetrahydro-5-oxo-2-furancarboxylic acid can be used for the mass production of the salt of amlopidine because it is nontoxic to the body and easy to handle.

Examples of the inert solvent suitable for the preparation of the salts of present invention include ethyl acetate, methanol, ethanol, isopropanol, acetonitrile, hexane, isopropyl ether and etc., with preference to ethyl acetate.

In the inert solvent, tetrahydro-5-oxo-2-furancarboxylic acid is used in the amount of 1-2 equivalents and preferably in the amount of 1.02-1.2 equivalents per equivalent of amlodipine. The reaction is performed at −5 to 30° C. and preferably at 0 to 15° C. for 5 to 40 hours and preferably for 15 to 30 hours.

According to the method of the present invention, amlodipine tetrahydro-5-oxo-2-furancarboxylate can be prepared at a yield of 90% or higher.

Also, the present invention encompasses a pharmaceutical composition useful in the treatment of ischemic cardiac disorders or hypertension, which comprises a therapeutically effective amount of amlodipine tetrahydro-5-oxo-2-furancarboxylate and a pharmaceutically acceptable diluent or carrier.

The composition of the present invention may be formulated into oral dosage forms including, but not limited to, granules, powders, solutions, tablets, capsules, dry syrup and the like, or parenteral dosage forms including injectables. The composition of the present invention is preferably formulated in the dosage form of tablets, capsules, solutions or injectables.

To be therapeutically effective, amlodipine tetrahydro-5-oxo-2-furancarboxylate is administered in the amount of 2–10 mg per day on the basis of the weight of amlodipine. In a unit dosage form, amlodipine tetrahydro-5-oxo-2-furancarboxylate is contained in the amount of 2.6–13.2 mg.

In practical use, amlodipine tetrahydro-5-oxo-2-furancarboxylate can be combined as the active ingredient in admixture with a pharmaceutically acceptable diluent or carrier selected from among excipients, disintegrants, binders, lubricants and mixtures thereof. The carrier may take a wide variety of forms depending on the form of the preparation desired for administration. In preparing the composition in a solid dosage form such as a tablet or a hard capsule, there may be employed microcrystalline cellulose, lactose, low-substituted hydroxycellulose and the like as an excipient; sodium starch glycollate, anhydrous monohydrogenphosphate and the like as a disintegrant; polyvinylpyrrolidone, low-substituted hydroxypropylcellulose, hydroxypropylcellulose and the like as a binder; and magnesium stearate, silica, talc and the like as a lubricant.

A formulation may comprise an additive to provide sheen to the tablet such as anhydrous dibasic calcium phosphate. To prevent atmospheric moisture from penetrating into the tablet, it may have a water-insoluble coating. The coating base must have a dense molecular structure and preferably, low solubility in water. Suitable for the base is a polymeric material selected from among methacrylic acid copolymer, hydroxypropylmethyl cellulose phthalate, cellulose acetate phthalate, hydroypropylmethylcellulose acetate succinate, polyvinyl alcohol and combinations thereof. Also, the coating may comprise conventional additives such as plasticizers, preservatives, coloring agents, light shielders, etc.

The composition of the present invention may be in the form of solutions such as sterile aqueous solution, or injectables. Such solution contains from 10 to 40% of propylene glycol and sodium chloride sufficient to avoid hemolysis (e.g. about 1% w/v).

A better understanding of the present invention may be obtained in light of the following examples which are set forth to illustrate, but are not to be construed to limit the present invention.

EXAMPLES

Amlodipine tetrahydro-5-oxo-2-furancarboxylate prepared according to the present invention was tested for various physical properties. First, the salt was formulated into tablets, capsules and aqueous solutions to test for the processability for dosage formation. Also, amlodipine tetrahydro-5-oxo-2-furancarboxylate was compared with known salts of amlodipine with regard to hydroscopicity, solubility, and chemical and light stability.

In the following reference examples, conventional salts of amlodipine were prepared according to methods disclosed in the art.

Reference Example 1

Preparation of Amlodipine Besylate

Amlodipine was prepared as disclosed in Korean Pat. Publication No. 87-809. The method described in Korean Pat. Publication No. 95-7228 was adopted to produce amlodipine besylate.

Reference Example 2

Preparation of Amlodipine Para-toluenesulfonate

In 100 ml of methanol was dissolved 20 g of para-toluenesulfonic acid. A solution of 40 g of the amlodipine prepared in Reference Example 1 in 500 ml of methanol was added dropwise to the methanol solution, followed by stirring at 23° C. for 3 hours.

After being filtered off, the solid thus produced was washed with 100 ml of methanol and 100 ml of n-hexane and dried in vacuo.

Reference Example 3

Preparation of Amlodipine Hydrochloride

To 100 ml of methanol was added 12 ml of conc-hydrochloric acid. A solution of 54 g of amlodipine prepared in Reference Example 1 in 500 ml of methanol was added dropwise, followed by stirring at 23° C. for 3 hours.

After being filtered off, the solid thus produced was washed with 100 ml of methanol and 100 ml of n-hexane and dried in vacuo.

Example 1

Preparation of Amlodipine (S)-Tetrahydro-5-oxo-2-furancarboxylate

Amlodipine (10 g, 0.025 mole) was dissolved in ethyl acetate (100 ml) with stirring. The solution was adjusted to 3° C. and slowly added with (S)-tetrahydro-5-oxo-2-furancarboxylic acid (3.69 g, 0.028 mole) prepared according to Korean Pat. Publication No. 0159540 to obtain a clear solution. This reaction was stirred at 3° C. for 20 hour to produce precipitates. They were filtered off and washed with ethyl acetate (50 ml), followed by drying at 40° C. under vacuum to give 12.4 g of the title compound (Yield 92.0%).

The element analysis and melting point of the amlodipine (S)-(+)-tetrahydro-5-oxo-2-furancarboxylate prepared above were determined.

TABLE 1

| | Element analysis for $C_{25}H_{31}N_2O_9Cl$ (%) | | | |
|---|---|---|---|---|
| Found | C: 55.0 | H: 5.9 | N: 5.1 | O: 25.9 |
| Calculated | C: 55.7 | H: 5.8 | N: 5.2 | O: 26.7 |

Melting point: 133° C. (measured by capillary melting point method with heating rate of about 1° C./minute)

Example 2

Preparation of Amlodipine (R)-Tetrahydro-5-oxo-2-furancarboxylate

The same procedure as in Example 1 was repeated, with the exception that (R)-tetrahydro-5-oxo-2-furancarboxylic acid was used instead of the (S)-type acid, to obtain 12.0 g of amlodipine (R)-tetrahydro-5-oxo-2-furancarboxylic acid (Yield 89.0%).

The element analysis and melting point of the amlodipine (R)-tetrahydro-5-oxo-2-furancarboxylate prepared above were determined.

TABLE 2

| | Element analysis for $C_{25}H_{31}N_2O_9Cl$ (%) | | | |
|---|---|---|---|---|
| Found | C: 55.2 | H: 5.9 | N: 5.1 | O: 25.8 |
| Calculated | C: 55.7 | H: 5.8 | N: 5.2 | O: 26.7 |

Melting point: 133° C. (measured by capillary melting point method with heating rate of about 1° C./minute)

Example 3

Preparation of Amlodipine Tetrahydro-5-oxo-2-furancarboxylic acid (Racemate)

The same procedure as in Example 1 was repeated, with the exception that racemic tetrahydro-5-oxo-2-furancarboxylic acid was used instead of (S)-tetrahydro-5-oxo-2-furancarboxylic acid, to obtain 12.2 g of racemic amlodipine tetrahydro-5-oxo-2-furancarboxylic acid (Yield 90.5%).

The racemic amlodipine tetrahydro-5-oxo-2-furancarboxylic acid prepared above was analyzed for element composition and measured for its melting point.

TABLE 3

| | Element analysis for $C_{25}H_{31}N_2O_9Cl$ (%) | | | |
|---|---|---|---|---|
| Found | C: 55.3 | H: 5.9 | N: 5.1 | O: 25.9 |
| Calculated | C: 55.7 | H: 5.8 | N: 5.2 | O: 26.7 |

Melting point: 133° C. (measured by capillary melting point method with heating rate of about 1° C./minute)

Example 4

Formulation of Tablet Containing Amlodipine Tetrahydro-5-oxo-2-furancarboxylate

The ingredients given in Table 4 were formulated to prepare a tablet containing amlodipine tetrahydro-5-oxo-2-furancarboxylate.

TABLE 4

| Ingredients | Contents (mg per tablet) |
|---|---|
| Amlodipine TOF | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowwon Machinery, and then the compressed material was formulated into tablets using a tableting machine from Erweka.

Example 5

Formulation of Tablet Containing Amlodipine Tetrahydro-5-oxo-2-furancarboxylate

The ingredients given in Table 5 were formulated to prepare a tablet containing amlodipine tetrahydro-5-oxo-2-furancarboxylate.

TABLE 5

| Ingredients | Contents (mg per tablet) |
|---|---|
| Amlodipine TOF salt | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and formulated into tablets using a tableting machine from Erweka.

Example 6

Formulation of Capsule Containing Amlodipine Tetrahydro-5-oxo-2-furancarboxylate

The ingredients given in Table 6 were formulated to prepare a capsule containing amlodipine tetrahydro-5-oxo-2-furancarboxylate.

TABLE 6

| Ingredients | Contents (mg per capsule) |
|---|---|
| Amlodipine TOF | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using using a roller press from Jowoon Machinery, and then the compressed material was filled into hard gelatin capsules using a capsule filling device from Bosche.

Example 7

Formulation of Capsule Containing Amlodipine Tetrahydro-5-oxo-2-furancarboxylate

The ingredients given in Table 7 were formulated to prepare a capsule containing amlodipine tetrahydro-5-oxo-2-furancarboxylate.

TABLE 7

| Ingredients | Contents (mg per capsule) |
|---|---|
| Amlodipine TOF | 5.0 based on Amlodipine |
| Lactose | 180 |
| Cross Povidone | 6 |
| Polyvinylpyrrolidone | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and filled in hard gelatin capsules using a capsule filling machine from Bosche.

Example 8

Test for Solubility of Amlodipine Tetrahydro-5-oxo-2-furancarboxylate

Solubilities of amlodipine tetrahydro-5-oxo-2-furancarboxylate prepared in Example 3 and amlodipine besylate prepared in Reference Example 1 in various solvents were measured at 37° C. The results are given in Table 8, below. The solubilities (mg/ml) of Table 8 are values based on the weight of amlodipine converted from the salts.

TABLE 8

| | Salts (mg/ml) | | |
|---|---|---|---|
| Solvents | TOF salt | Besylate | Note |
| Dist. Water | 520 | 2.00 | Ionic Strength 0.2 buffer |
| pH 3 | 400≦ | 3.25 | Dissolved at 37° C. |
| pH 4 | 400≦ | 3.15 | |
| pH 6 | 400≦ | 3.19 | |
| pH 7 | 400≦ | 1.59 | |
| pH 8 | 400≦ | 1.39 | |

As seen in Table 8, solubilities of amlodipine tetrahydro-5-oxo-2-furancarboxylate in distilled water and buffers of various pH are approximately 400 times or more greater than those of amlodipine besylate. That is, amlodipine tetrahydro-5-oxo-2-furancarboxylate shows far superior solubility properties over amlodipine besylate.

Example 9

Test for Stability of Amlodipine Tetrahydro-5-oxo-2-furancarboxylate

1. Chemical Stability of Amoldipine Tetrahydro-5-oxo-2-furancarboxylate in Solid State Amlodipine tetrahydro-5-oxo-2-furancarboxylate prepared in Example 3 and amlodipine besylate prepared in Reference Example 1 were subjected to accelerated test at 60° C. and the results are summarized in Table 9, below.

TABLE 9

| Salts | Storage Period | | | |
|---|---|---|---|---|
| | initial | 1 week | 2 weeks | 4 weeks |
| TOF | 99.7% | 99.7% | 99.3% | 99.1% |
| Besylate | 99.6% | 99.6% | 99.4% | 99.2% |

As shown in Table 9, there were virtually no changes in the content of amlodipine tetrahydro-5-oxo-2-furancarboxylate, like amlodipine besylate, as measured by accelerated test at 60° C. The data of Table 9 demonstrate that, comparable to that of amlodipine besylate, the chemical stability of amlodipine tetrahydro-5-oxo-2-furancarboxylate is excellent with regard to temperature.

2. Chemical Stability of Amlodipine Tetrahydro-5-oxo-2-furancarboxylate in Aqueous State To investigate the stability in an aqueous state, mlodipine tetrahydro-5-oxo-2-furancarboxylate prepared in Example 3 and amlodipine besylate prepared in Reference Example 1 were separately dissolved in distilled water. The resulting aqueous solutions were stored at 25° C. for 4 weeks in the dark, after which a measurement was made of the contents of the salts with resort to HPLC under the same conditions as in the solid state.

The results of the light-shielded stability test indicate that neither degraded impurity nor content change was found in both amlodipine tetrahydro-5-oxo-2-furancarboxylate and amodipine besylate.

Example 10

Test for Light Stability of Amlodipine Tetrahydro-5-oxo-2-furancarboxylate

Amlodipine tetrahydro-5-oxo-2-furancarboxylate prepared in Example 3, amlodipine besylate and other salts of amlodipine prepared in Reference Examples 1 to 3 were stored for four weeks at 25° C. with exposure to daylight. A measurement was made of the contents of the salts with resort to HPLC under the same conditions as in the chemical stability test. The results are given in Table 10, below.

TABLE 10

| Salts | Initial Content (HPLC) | Stored 4 weeks, 25° C. daylight Content (HPLC) |
|---|---|---|
| TOF | 99.5% | 98.0% |
| Besylate | 99.2% | 82.5% |
| Tosylate | 99.2% | 72.0% |
| Hydrochloride | 99.0% | 60.5% |

As apparent from Table 10, a smaller reduction in content was found in amlodipine tetrahydro-5-oxo-2-furancarboxylate than in the other salts of amlodipine, It was also found that amlodipine besylate turned yellow from white while amlodipine tetrahydro-5-oxo-2-furancarboxylate showed no color change. These data accordingly show that amlodipine tetrahydro-5-oxo-2-furancarboxylate is superior in light stability to amlodipine besylate and thus is very advantageous in application for anti-hypertensives which are usually used for a long period of time.

Taken together, the data presented in the above examples indicate that the amlodipine tetrahydro-5-oxo-2-furancarboxylate of the present invention has excellent physicochemical properties including hygroscopicity, chemical and light stability, solubility and processability for dosage formulation. Especially, with high solubility, amlodipine tetrahydro-5-oxo-2-furancarboxylate is easy to deliver in the body of a patient. In addition, this salt can be stored for a long period of time due to its superior light stability.

What is claimed is:

1. A tetrahydro-5-oxo-2-furancarboxylic acid salt of amlodipine.

2. The tetrahydro-5-oxo-2-furancarboxylic acid salt of amlodipine as defined in claim 1, wherein the tetrahydro-5-oxo-2-furancarboxylic acid is (S)-tetrahydro-5-oxo-2-furancarboxylic acid or (R)-tetrahydro-5-oxo-2-furancarboxylic acid.

3. A method for preparing amlodipine tetrahydro-5-oxo-2-furancarboxylate, in which amlodipine is reacted with tetrahydro-5-oxo-2-furancarboxylic acid in an inert solvent.

4. The method as defined in claim 3, wherein the tetrahydro-5-oxo-2-furancarboxylic acid is (S)-tetrahydro-5-oxo-2-furancarboxylic acid or (IR)-(−)-10-tetrahydro-5-oxo-2-furancarboxylic acid.

5. A pharmaceutical composition for the treatment of ischemic cardiac disorders or hypertension, comprising a therapeutically effective amount of the tetrahydro-5-oxo-2-furancarboxylic acid salt of amlodipine of claim 1, and a pharmaceutically acceptable diluent or carrier.

6. The pharmaceutical composition as defined in claim 5, wherein the composition is in the dosage form of tablets or capsules.

7. The pharmaceutical composition as defined in claim 5, wherein the composition is in the dosage form of solutions or injectables.

8. A pharmaceutical composition for the treatment of ischemic cardiac disorders or hypertension, comprising a therapeutically effective amount of the tetrahydro-5-oxo-2-furancarboxylic acid salt of amlodipine of claim 2, and a pharmaceutically acceptable diluent or carrier.

9. The pharmaceutical composition as defined in claim 8, wherein the composition is in the dosage form of tablets or capsules.

10. The pharmaceutical composition as defined in claim 8, wherein the composition is in the dosage form of solutions or injectables.

* * * * *